(12) United States Patent
Kobayashi

(10) Patent No.: US 7,029,437 B2
(45) Date of Patent: Apr. 18, 2006

(54) ELECTRONIC ENDOSCOPE APPARATUS

(75) Inventor: Hiroyuki Kobayashi, Saitama (JP)

(73) Assignee: PENTAX Corporation, Tokyo (JP)

( * ) Notice: Subject to any disclaimer, the term of this patent is extended or adjusted under 35 U.S.C. 154(b) by 176 days.

(21) Appl. No.: 10/693,883

(22) Filed: Oct. 28, 2003

(65) Prior Publication Data

US 2004/0092792 A1    May 13, 2004

(30) Foreign Application Priority Data

Oct. 31, 2002    (JP) .......................... P2002-317473

(51) Int. Cl.
*A61B 1/06* (2006.01)
(52) U.S. Cl. ...................... 600/180; 600/160
(58) Field of Classification Search ................ 600/103, 600/118, 160, 178–180; 348/68–69, 297, 348/687–688
See application file for complete search history.

(56) References Cited

U.S. PATENT DOCUMENTS

| 5,475,420 A * | 12/1995 | Buchin .......................... 348/72 |
| 6,080,104 A * | 6/2000 | Ozawa et al. ................ 600/180 |
| 6,475,141 B1 * | 11/2002 | Abe ............................. 600/180 |
| 6,765,619 B1 * | 7/2004 | Deng et al. .................. 348/362 |
| 6,914,630 B1 * | 7/2005 | Nakamura ................... 348/296 |

OTHER PUBLICATIONS

U.S. Appl. No. 10/663,788 to Kobayashi et al., filed Sep. 17, 2003, and entitled "Diagnosis Supporting Device".
U.S. Appl. No. 10/260,335 to Iida et al., filed Oct. 1, 2002 and entitled "Electronic Endoscope With Light-Amount Adjustment Apparatus".

* cited by examiner

*Primary Examiner*—John P. Leubecker
*Assistant Examiner*—Philip R. Smith
(74) *Attorney, Agent, or Firm*—Greenblum & Bernstein, P.L.C.

(57) ABSTRACT

An electronic endoscope apparatus has a light source, a pixel luminance detector, a division setter, an average block luminance calculator, a peak-luminance determiner, a representative luminance calculator, and a brightness adjuster. The division setter divides the subject image into a plurality of blocks composed of given pixels. The average block luminance calculator calculates a plurality of average block-luminance-levels. The peak-luminance determiner compares the average block-luminance-levels with each other in order to determine a substantially maximum average block-luminance-level from the plurality of average block-luminance-levels as a peak luminance level. The representative luminance calculator calculates a representative luminance level indicating a brightness of the subject image. The brightness adjuster adjusts the brightness of the subject image in accordance with the representative luminance level.

15 Claims, 12 Drawing Sheets

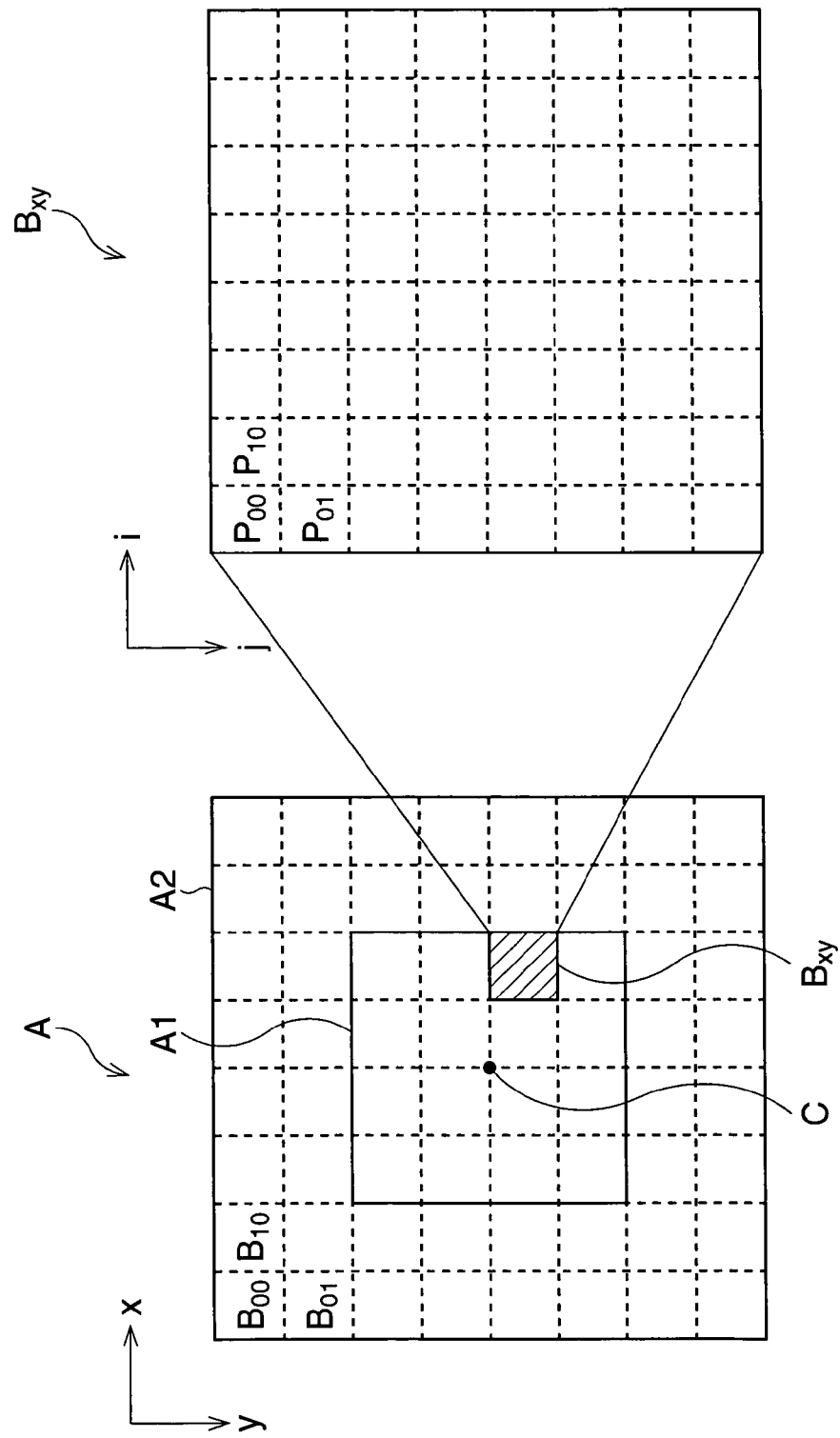

<ONE HIGH LUMINANCE PIXEL>

<PLURAL HIGH LUMINANCE PIXELS>

ELECTRONIC ENDOSCOPE APPARATUS

BACKGROUND OF THE INVENTION

1. Field of the Invention

The present invention relates to an electronic endoscope apparatus having a video-scope with an image sensor and a video-processor, and especially relates to a brightness adjustment process for a subject image displayed on a monitor.

2. Description of the Related Art

In an electronic endoscope apparatus, image-pixel signals are read from an image sensor provided at a tip portion of a video-scope, and a luminance level indicating the brightness of a displayed subject image is calculated from the image-pixel signals. Then,based on a difference between the luminance level and a reference level indicating a proper brightness of the subject image, the brightness of the subject image is adjusted so as to maintain a proper brightness. For example, the amount of light for illuminating the subject is adjusted by a diaphragm, whereas exposure time at the image sensor is adjusted by using an electronic shutter function.

Generally, to measure brightness, an average metering that calculates an average brightness or a peak metering that determines a relatively high luminance level in the subject image as a peak luminance level, is applied. The operator selects the metering method in accordance with the situation.

When the tip portion of the video-scope is extremely close to the observed portion, or when a tip portion of a metallic disposition tool, such as a forceps, extends over the tip surface of the video-scope so that a tip portion image is displayed, a so called "halation" can be generated in the peripheral area of the screen, wherein a white color image is displayed. Therefore, when the halation is generated on the peripheral area in a situation where the peak metering is applied, the brightness adjustment is performed so as to lower the luminance level even if the total brightness of the subject image is proper. One method for preventing this problem is to set the peak metering-area to an area around the center portion of the display-screen, whereas the average metering-area is set to the peripheral area.

However, because of a mucous membrane or an uneven surface of the observed portion, a luminance level of a minute area in the screen can become extremely high compared with the surrounding area. When such a minute area with a high luminance level is located at the center portion, the peak luminance level is calculated in accordance with the minute area so that the brightness adjustment process is performed so as to lower the luminance level. This adjustment process is an obstacle to proper the operation or treatment.

SUMMARY OF THE INVENTION

Therefore, an object of the present invention is to maintain the brightness of the subject properly regardless of the existence of minute areas with high luminance levels.

An electronic endoscope apparatus according to the present invention has a video-scope with an image sensor and a video-processor. The electronic endoscope apparatus has a light source, a pixel luminance detector, a division setter, an average block luminance calculator, a peak-luminance determiner, a representative luminance calculator, and a brightness adjuster. The light source radiates light for illuminating a subject. The pixel luminance detector detects the luminance level of each pixel in a plurality of pixels, which forms a subject image displayed on a display, in accordance with image-pixel signals read from the image sensor. Herein, the subject image is an image to be displayed and observed.

The division setter divides the subject image into a plurality of blocks composed of given pixels. The average block luminance calculator calculates a plurality of average block-luminance-levels. Each of the plurality of average block-luminance-levels indicates a substantial average luminance level of each corresponding block and is calculated from a plurality of luminance levels of pixels arranged in corresponding block. In the present invention, the expression "substantial average" does not only mean a mathematically and strictly defined average. This expression includes the meaning of values obtained by considering a plurality of pixels in the block and utilizing the values of luminance levels corresponding to the plurality of pixels. The peak-luminance determiner compares the average block-luminance-levels with each other in order to determine a substantially maximum average block-luminance-level from the plurality of average block-luminance-levels as a peak luminance level. For example, an actual maximum average block-luminance-level may be determined as the peak luminance level. On the other hand, when a plurality of blocks exists, each of which is less than a maximum average block-luminance-level and has a relatively high average block-luminance-level, the average block-luminance-level corresponding to the a plurality of blocks may be determined as the peak luminance level.

The representative luminance calculator calculates a representative luminance level indicating the brightness of the subject image. The brightness adjuster adjusts the brightness of the subject image in accordance with the representative luminance level. Note that, the size and pixel number of a block is defined so as to encompass a minute area with a high luminance level. For example, the pixel number is defined to be from 30 to 120 in each block.

For example, the brightness adjuster adjusts an amount of light radiated from the light source toward the subject so as to maintain a proper brightness, or the brightness adjuster adjusts an exposure time at the image sensor so as to maintain a proper brightness.

For example, an electronic endoscope apparatus has a peak metering-area setter that sets a peak metering-area around a center portion of the subject image. The peak-luminance determiner determines the peak luminance level in accordance with blocks included in the peak metering-area. When the forceps is used, the electronic endoscope apparatus may have a treatment tool detector that detects the use of a treatment tool utilizing a treatment tool tube provided in the video-scope. The peak metering-area setter sets the peak metering-area so as to exclude a tool displaying area, in which a tip portion of the treatment tool is displayed.

For example, the electronic endoscope apparatus also has an average metering-area setter that sets an average metering-area in the subject image so as to include at least a peripheral portion of the subject image; and an average luminance calculator that calculates an average luminance level indicating a substantial average luminance level, in accordance with blocks included in the average metering-area. The peak-luminance determiner determines the peak luminance level in accordance with blocks included in the peak metering-area, and the representative luminance calculator calculates the representative luminance level in accordance with the peak luminance level and the average luminance level. For example, the representative luminance calculator multiplies the peak luminance level by a peak weighted coefficient and multiplies the average luminance level by an average weighted coefficient to obtain the representative luminance level.

On the other hand, the electronic endoscope apparatus may have a peak metering-area setter that sets a first peak metering-area around a center portion of the subject image, and sets a second peak metering-area so as to surround the first peak metering-area. The peak-luminance determiner determines a first peak luminance level in accordance with blocks included in the first peak metering-area, and determines a second peak luminance level in accordance with blocks included in the second peak metering-area, and the representative luminance calculator calculates the representative luminance level in accordance with the first and second peak luminance levels. For example, the division setter sets a first plurality of blocks composed of a first number of pixels, and sets a second plurality of blocks composed of a second number of pixels, which is more than the first number of pixels. The division setter sets the second plurality of blocks in the first peak metering-area or the second peak metering-area. For example, the representative luminance calculator multiplies the first peak luminance level by a first peak weighted coefficient and multiplies the second peak luminance level by a second peak weighted coefficient to obtain the representative luminance level, and the first peak weighted coefficient is larger than the second peak weighted coefficient.

The electronic endoscope apparatus has, for example, an average metering-area setter that sets an average metering-area in the subject image so as to include at least a peripheral portion of the subject image; and an average luminance calculator that calculates an average luminance level indicating a substantial average luminance level in accordance with blocks included in the average metering-area. The representative luminance calculator calculates the representative luminance level in accordance with the first peak luminance level, the second peak luminance level, and the average luminance level.

The division setter, for example, sets the a plurality of blocks such that each block is substantially the same size and has substantially the same number of pixels, or sets a plurality of different types of blocks, each of which is different from an other type of block with respect to at least one of the number of pixels and the size.

An automatic brightness adjustment apparatus for endoscope according to another aspect of the present invention has a pixel luminance detector, an average block luminance calculator, a peak-luminance determiner, a representative luminance calculator, and a brightness adjuster. The pixel luminance detector detects luminance levels in each of plural pixels, which form a subject image displayed on a display, in accordance with image-pixel signals read from an image sensor, which is provided in a video-scope. The average block luminance calculator calculates a plurality of average block-luminance-levels for a plurality of blocks, which is defined by dividing the subject image. Each of the plurality of average block-luminance-levels indicates a substantial average luminance level of a block and is calculated from a plurality of luminance levels of pixels arranged in corresponding block. The peak-luminance determiner compares the average block-luminance-levels with each other to determine a substantially maximum average block-luminance-level from the plurality of average block-luminance-levels as a peak luminance level. The representative luminance calculator calculates a representative luminance level indicating a brightness of the subject image. The brightness adjuster adjusts the brightness of the subject image in accordance with the representative luminance level.

A method for adjusting a brightness of a displayed subject image according to another aspect of the present invention has steps of: 1) detecting luminance levels in each of plural pixels, which form a subject image displayed on a display, in accordance with image-pixel signals read from an image sensor, which is provided in a video-scope; 2) calculating a plurality of average block-luminance-levels for a plurality of blocks, which is defined by dividing the subject image, each of the plurality of average block-luminance-levels indicates a substantial average luminance level of a block and is calculated from a plurality of luminance levels of pixels arranged in corresponding block; 3) comparing the average block-luminance-levels with each other to determine a substantially maximum average block-luminance-level from the plurality of average block-luminance-levels as a peak luminance level; 4) calculating a representative luminance level indicating a brightness of the subject image; and 5) adjusting the brightness of the subject image in accordance with the representative luminance level.

BRIEF DESCRIPTION OF THE DRAWINGS

The present invention will be better understood from the description of the preferred embodiment of the invention set fourth below together with the accompanying drawings, in which:

FIG. 3 is a view showing a metering-area of an observed image;

DESCRIPTION OF THE PREFERRED EMBODIMENTS

Hereinafter, the preferred embodiments of the present invention are described with reference to the attached drawings.

Figure 1:
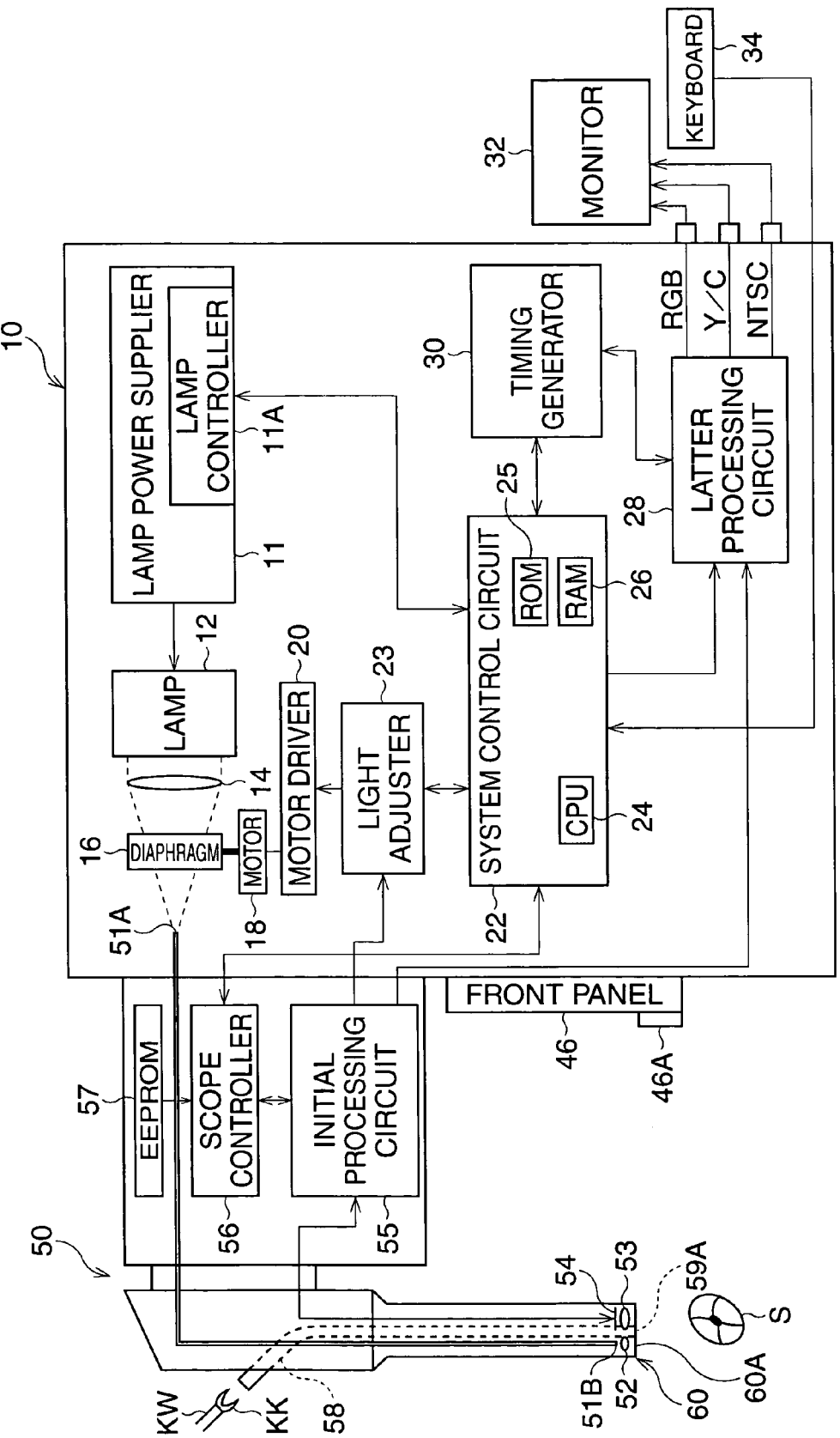
FIG. 1 is a block diagram of an electronic endoscope apparatus according to a first embodiment.

FIG. 1 is a block diagram of an electronic endoscope apparatus according to the first embodiment.

The electronic endoscope apparatus has a video-scope 50 with a CCD 54 and a video-processor 10. The video-scope 50 is detachably connected to the video-processor 10, and further a TV monitor 32 and a keyboard 34 are connected to the video-processor 10.

When a lamp switch provided on the video-processor 10 (not shown) is turned ON, electric power is supplied from a lamp power supplier 11 including a lamp controller 11A to a lamp 12, so that light is emitted from the lamp 12 and is directed toward an incident surface 51A of a fiber-optic bundle 51 via a collecting lens 14 and a diaphragm 16. The fiber-optic bundle 51, provided through the video-scope 50, directs the light toward the tip portion 60 of the video-scope 50.

The light passing through the fiber-optic bundle 51 exits from the end surface 51B of the fiber-optic bundle 51 and is emitted toward a subject S via a diffusion lens 52, so that the subject S is illuminated. Further, a forceps tube 58 is provided in the video-scope 50. When treating or operating on an observed portion, a forceps KW with a metallic treatment tool KK is inserted into the forceps tube 58.

The light reflected on the subject S passes through an objective lens (53) and reaches the CCD 54, so that an image is formed on a photo-sensor area of the CCD 54. For the color imaging process, in this embodiment, an on-chip color filter method using one chip color filter is applied. A color filter, checkered by four color elements of Yellow (Ye), Magenta (Mg), Cyan (Cy), and Green (G), is arranged on the photo-sensor area of the CCD 54 such that the four color elements are opposite to the pixels arranged in the photo-sensor area. Analog image-pixel signals, corresponding to the light passing through the color filter, are generated in the CCD 54 by the photoelectric transform effect. The generated color image-pixel signals are composed of plural color signal components.

Then, one field worth of image-pixel signals is read from the CCD 54 at regular time intervals in accordance with the so called "color difference line sequential system". In this embodiment, the NTSC standard is used as the color TV standard, accordingly, one field worth of image-pixel signals is read from the CCD 54 at 1/60 second time intervals, and then is fed to an initial processing circuit 55.

In the initial processing circuit 55, a preamplifier, sample-hold circuit, memory, an image processing circuit, and soon, are included. Various processes, such as white balance process, gamma process, and so on, are performed for the image-pixel signals, which are then converted to digital image signals. The digital image signals are temporarily stored in the memory and then fed to a latter processing circuit 28 in the video-processor 10. Further, luminance signals obtained from the image-pixel signals are fed to a light-adjuster 23 in the video-processor 10 at 1/60 second intervals corresponding to the NTSC standard.

In the latter processing circuit 28, a given process is performed for the image signals, and the image signals are converted to video signals, such as S-video signals; R, G, B component signals; and NTSC composite signals. The video signals are fed to the monitor 32. Thus, the subject image is displayed on the monitor 32.

The system control circuit 22 including a CPU 24, a ROM 25, and a RAM 26 controls the video-processor 10, and feeds control signals to the light adjuster 23, the latter processing circuit 28, and so on. The timing generator 30 outputs clock pulses for adjusting a signal processing timing to each circuit, and feeds synchronized signals accompanying the video signals, to the latter processing circuit 28.

The diaphragm 16, provided between the incident surface 51A of the fiber-optic bundle 51 and the collecting lens 16, is driven for adjusting the amount of light illuminating the subject S, and it is opened and closed by driving a motor 18. The light-adjuster 23, which is constructed of a DSP (Digital Signal Processor), controls the drive of the diaphragm 16, to adjust the light-amount. The light-adjuster 23 outputs control signals to a motor driver 20, and the motor driver 20 outputs a driving signal to the motor 18 so that the diaphragm 16 is opened or closed by a given-amount. In this embodiment, as described later, a subject image to be observed is divided into a plurality of blocks, and an average metering and a peak metering are performed to calculate a representative luminance level indicating a brightness of the subject image. Then, the light-adjuster 23 controls the brightness of the subject image so as to maintain the proper brightness of the subject image displayed on the monitor 32.

In the video-scope 50, a scope-controller 56 and an EEPROM 57 are provided. The scope-controller 56 controls the video-scope 50, and the EEPROM 57 storing data associated with the video-scope 50. The data stored in the EEPROM 57 includes the number of pixels and the position of the forceps outlet 59A on the tip surface 60A. The scope-controller 56 reads the data from the EEPROM 57, and outputs control signals to the initial processing circuit 55. When the video-scope 50 is connected to the video-processor 10, the data is transmitted between the video-scope 50 and the video-processor 10.

A switch 46A for setting a reference luminance level, which indicates a standard luminance level with respect to the light-adjustment process, is provided on a front panel 46. An operation signal is fed to the system control circuit 22 when the switch 46A is operated. The predetermined reference luminance level is temporarily stored in the RAM 26 as data and the reference luminance level data is fed to the light-adjuster 23.

Figure 2:
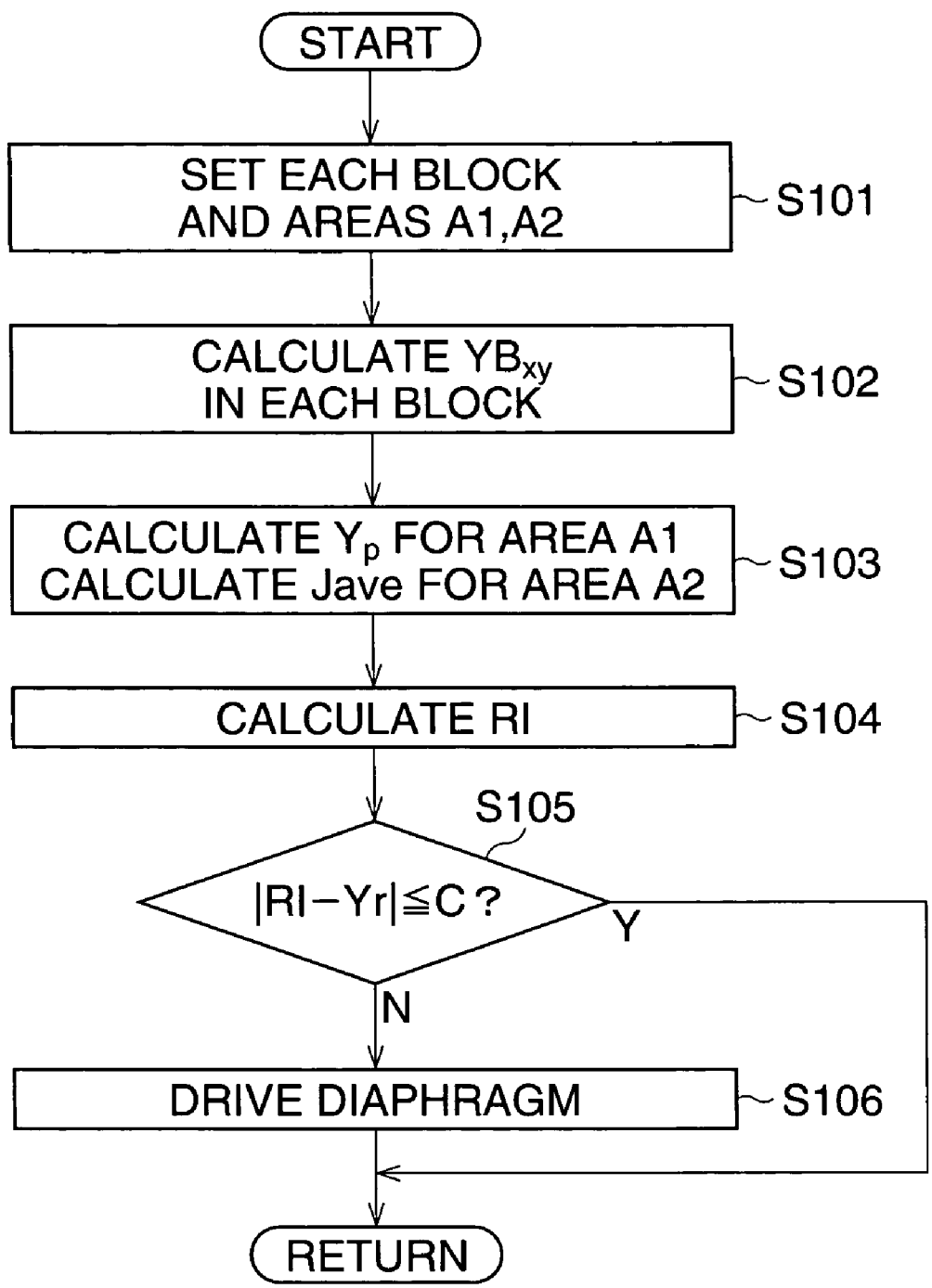
FIG. 2 is a flowchart showing an automatic light-amount adjustment process.
Figure 4A:
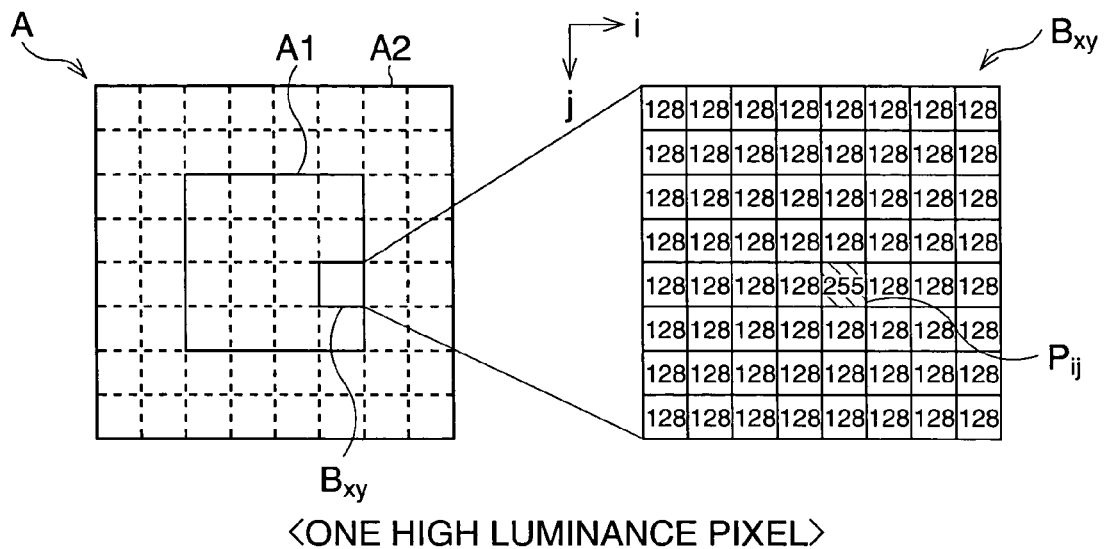
FIGS. 4A and 4B are views showing an observed image wherein a minute high-luminance-level area exists.
Figure 4B:
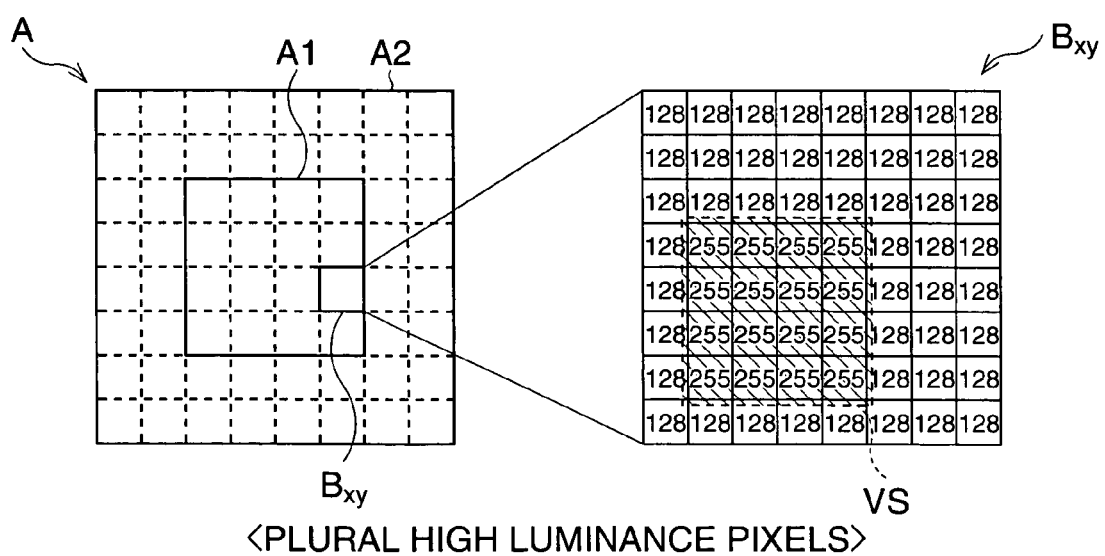

FIG. 2 is a flowchart showing an automatic light-amount adjustment process, which is performed by the light-adjuster 23, and is performed in 1/60 second intervals in accordance with the NTSC method. FIG. 3 is a view showing a metering-area of an observed image, and FIGS. 4A and 4B are views showing observed image wherein a minute high-luminance-level area exists. Note that, the number of pixels of the CCD 54 is smaller than that of the monitor 32. Then, a subject image formed on the CCD 54 is substantially and directly displayed on the monitor 32 without a down sampling process or an interpolation process.

In Step S101, as shown in FIG. 3, a subject image to be observed (hereinafter, called the observed image) "A" is divided into a plurality of blocks $B_{xy}$, and then a peak metering-area "A1" corresponding to the peak metering and an average metering-area "A2" corresponding to the average metering are defined. Note that, in the actual process, the light-adjuster 23 defines the plurality of blocks $B_{xy}$ based on a memory provided therein.

The observed image "A" corresponds to a subject image displayed on the monitor 32, and is constructed of 8×8 (=64) blocks $B_{xy}$ (x=0 to 7, y=0 to 7) arranged in a matrix. Herein, the suffix "x" indicates the horizontal direction on the screen of the monitor 32, and the suffix "y" indicates the vertical direction on the screen. Further, each block $B_{xy}$ is constructed of 8×8=64 pixels $P_{ij}$ (x=0 to 7, y=0 to 7). The suffix "i" indicates the horizontal direction of the screen, and the suffix "j" indicates the vertical direction of the screen. Each pixel $P_{ij}$ has a luminance level $Y_{ij}$, the value or magnitude of which is defined in accordance with a corresponding luminance signal fed from the video-scope 50. The brightness of the observed image is represented by 256 levels, and the magnitude of a luminance level is represented by one integer from "0" to "255".

The peak metering-area "A1" for performing the peak metering is defined around the center portion of the observed image A so as to include the center position "C". The average metering-area "A2" for performing the average metering corresponds to the total area of the observed image "A". The ratio of the average metering-area "A2" to the peak metering-area A1 is herein "1 to 3".

Since an organ such as colon has a duct-shape, the inner wall of the organ, which is close to the tip surface 60A, is displayed on the peripheral portion of the screen, namely, the image of the inner wall appears on the peripheral area of the observed image "A". Further, when the treatment tool KW is used, the metallic tip portion KK of the treatment tool KW is displayed on the peripheral portion of the screen. Namely, the image of the tip portion KK partially appears on the peripheral area of the observed image "A".

Since the metallic tool tip portion KK or the subject close to the tip surface 60A of the video-scope 50 is displayed in the peripheral area, a halation occasionally occurs in the peripheral area. Accordingly, as shown in FIG. 3, the peak metering-area "A1" does not include the peripheral area of the observed image "A". Thus, the operator can observe the desired portion, which is in the center portion, with a relatively high-luminance level. After Step S101 is performed, the process goes to Step S102.

In Step S102, based on the following formula, an average luminance level (hereinafter, called "average block-luminance-level") $YB_{xy}$ is calculated for each block $B_{xy}$, so that 64 average block-luminance-levels $YB_{xy}$ are calculated.

$$YB_{xy} = \Sigma Y_{ij}/(i \times j) \quad (1)$$

In Step S103, an average luminance level $J_{ave}$ is calculated relative to the average metering-area "A2", and a peak luminance level $Y_p$ is calculated relative to the peak metering-area "A1".

The average luminance level $J_{ave}$ is calculated from 64 average block-luminance-levels $YB_{xy}$ in accordance with the following formula.

$$J_{ave} = \Sigma YB_{xy}/x \times y \quad (2)$$

On the other hand, in the case of peak luminance level $Y_p$, a maximum average block-luminance-level among the 64 average block-luminance-levels $YB_{xy}$ is selected by comparing the average block-luminance-levels $YB_{xy}$ with each other.

In Step 104, the representative luminance level RI of the observed image "A" is calculated in accordance with the following formula. Note that, α, β respectively indicate weighted coefficients.

$$RI = \alpha \times J_{ave} + \beta \times Y_p \quad (3)$$

The values of weighted coefficients α, β are preset in accordance with the situation. Herein, the value of the coefficient α is sufficiently small compared to the value of the coefficient β.

In Step S105, it is determined whether a difference between the representative luminance level RI and the reference luminance level $Y_r$ is larger than the allowable difference "C". When it is determined that the difference between the representative luminance level RI and the reference luminance level "$Y_r$" is larger than the allowable difference "C", the process goes to Step S106, wherein a control signal corresponding to the difference is fed from the light-adjuster 23 to the motor driver 20. Thus, the diaphragm 16 is driven by a given amount corresponding to the difference such that the brightness of the displayed subject image is proper. After Step S106 is performed, the process is terminated.

On the other hand, when it is determined that the difference between the representative luminance level RI and the reference luminance level $Y_r$ is not larger than the allowable difference "C", namely, the representative luminance level RI substantially coincides with the reference luminance level $Y_r$, the process is directly terminated.

In FIG. 4A, an observed image with one high-luminance pixel is shown. In this situation, the portion to be observed is displayed within the peak metering-area "A1", and one pixel $P_{ij}$ (i=j=4) in the block $YB_{mn}$ ($0 \leq m \leq 7$, $0 \leq n \leq 7$) has a high luminance level (=255) due to the mucous membrane or the minute uneven surface of the observed portion, whereas each of the other pixels has a luminance level which is the same as the reference luminance level (=128). In this case, an average block-luminance-level $YB_{mn}$ is firstly calculated from 64 pixels arranged in the block $B_{mn}$, and the peak luminance level $Y_p$ is determined by comparing the calculated average block-luminance-levels $YB_{xy}$ to each other. In other words, the luminance level of the pixel $P_{44}$ is not directly determined as the peak luminance level $Y_p$ but is determined on the basis of the pixel $P_{44}$ and the other pixels having a reference luminance level.

On the other hand, as shown in FIG. 4B, even if pixels constructing a minute area "VS" have respectively high luminance levels, the average block-luminance-level $YB_{xy}$ is calculated in each block, and the peak luminance level $Y_p$ is calculated in accordance with the plurality of average block-luminance-levels $YB_{xy}$. Namely, the peak luminance level $Y_p$ is not determined due to only the minute area "VS".

In this way, in the first embodiment, the average block-luminance-level $YB_{xy}$ is calculated in each block $B_{xy}$, and the peak luminance level $Y_p$ is determined from the plurality of average block-luminance-levels $YB_{xy}$ which correspond to blocks arranged in the peak metering-area "A1". On the other hand, the $J_{ave}$ is calculated from the average block-luminance-levels $YB_{xy}$ corresponding to blocks arranged in the average metering-area "A2". Then, the representative luminance level RI is calculated in accordance with the average luminance level $J_{ave}$ and the peak luminance level $Y_p$, and the diaphragm 16 is driven on the basis of the difference between the representative luminance level RI and the reference luminance level $Y_r$.

The peak luminance level $Y_p$ may be directly determined as the representative luminance level RI by setting α to "0". The peak metering-area "A1" may be defined in another area different from the area A1 shown in FIG. 3. For example, the total area may be defined as the peak metering-area "A1". The average metering-area "A2" may be defined as only the peripheral area of the screen so as not to include the peak metering-area "A1".

In this embodiment, the setting of the metering-area "A1", "A2", and the block $B_{xy}$ is performed in the initial process in the automatic light-amount adjustment process, however, the above processes may be performed in the initial setting soon after the electric power is turned ON.

The peak metering-area may be set to another area different from the area "A1" so as to include a center portion of the object image.

The size or number of pixels in the blocks $B_{xy}$ may be different from that shown in FIG. 3.

The amount of light emitted from the lamp 11 may be directly controlled by adjusting an emitting-amount of the lamp 11, instead of the use of the diaphragm 16.

When the number of pixels of the CCD 54 is larger than that of the monitor 32, the automatic light-amount adjustment process may be performed in accordance with the pixels forming the subject image to be displayed on the monitor 32. The subject image may be formed by an image process, such as a down sampling.

The average block-luminance-level may be calculated on the basis of the luminance level distribution. For example, each pixel level is multiplied by a corresponding pixel number, and the sum of the multiplied values is divided by the total pixel number.

Figure 5:
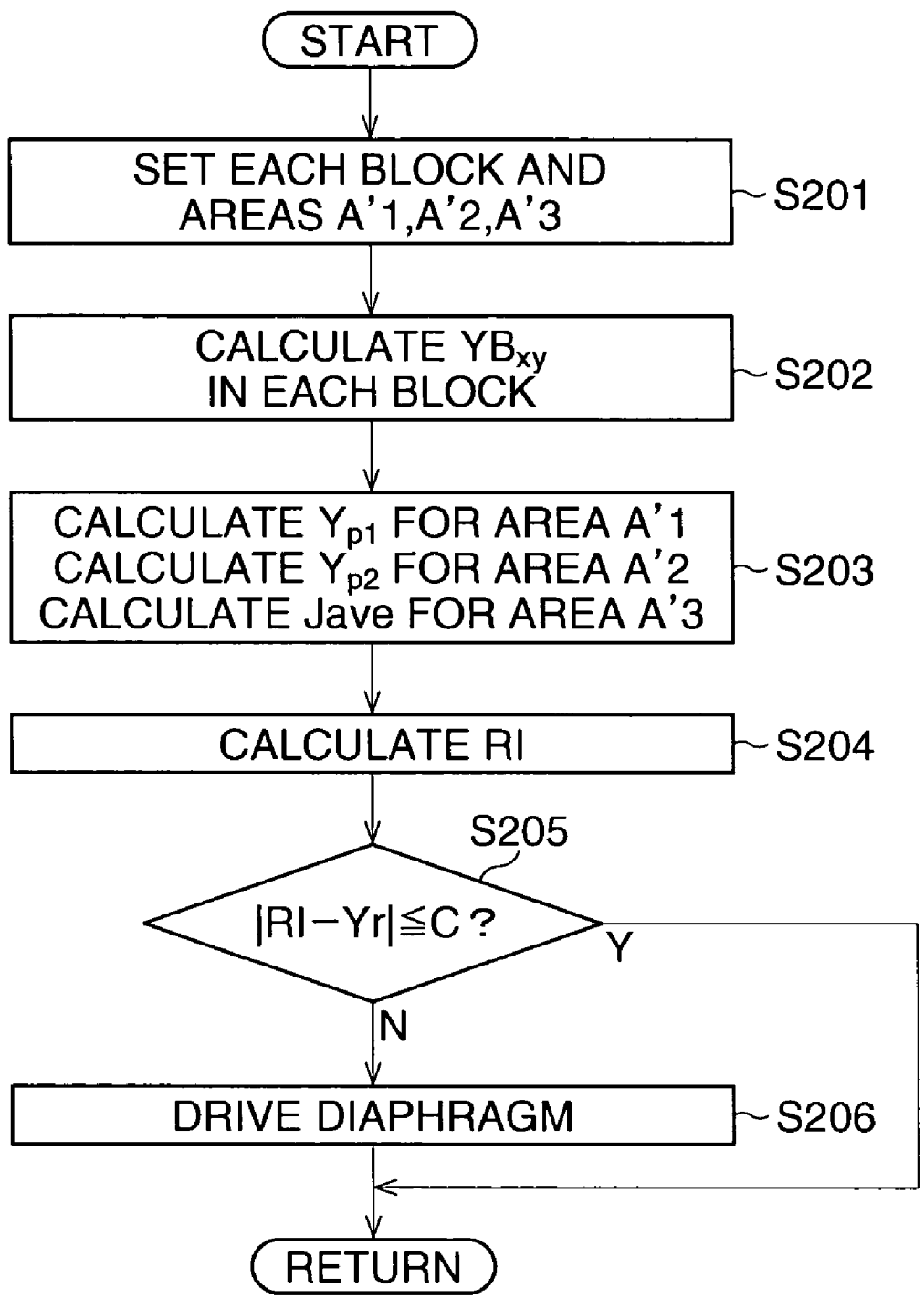
FIG. 5 is a view showing an automatic light-amount adjustment process according to a second embodiment.
Figure 6:
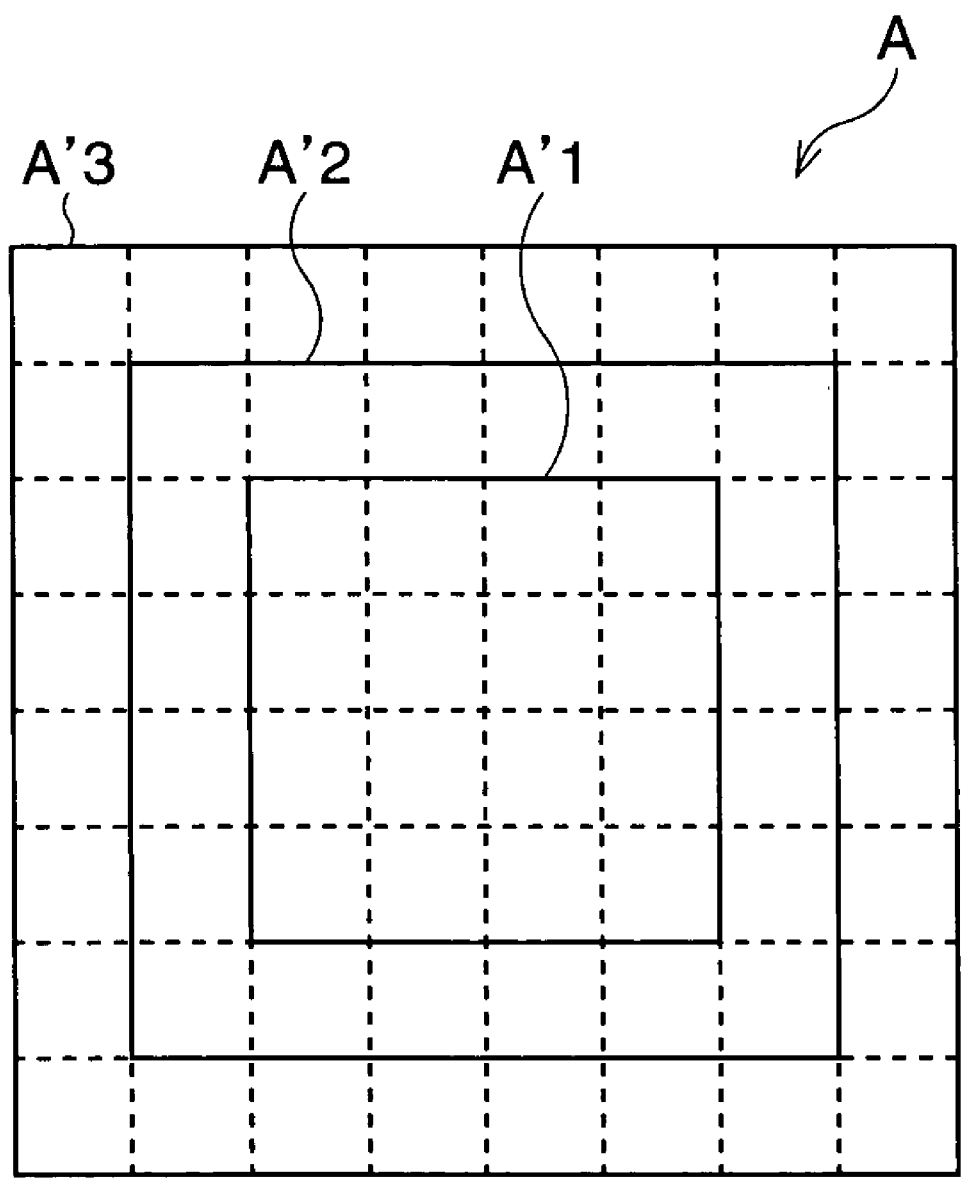
FIG. 6 is a view showing an observed image according to the second embodiment.

FIGS. 5 and 6 show an electronic endoscope apparatus of a second embodiment. The second embodiment is different from the first embodiment in that two peak metering-areas are defined.

FIG. 5 is a view showing an automatic light-amount adjustment process according to the second embodiment. FIG. 6 is a view showing an observed image according to the second embodiment.

In Step S201, the observed image A is divided into a plurality of blocks $B_{xy}$, and further a first peak metering-area "A'1", a second peak metering-area "A'2", and an average metering-area "A'3" are defined.

As shown in FIG. 6, the first peak metering-area "A'1" is defined around the center of the observed image "A", and the rectangular-shaped second peak metering-area "A'2" is defined so as to surround the first peak metering-area "A'1". Further, the average metering-area "A'3" is defined as an area, which is formed by excluding the areas "A'1" and "A'2" from the total area of the observed image "A".

In Step S202, the average block-luminance-level $YB_{xy}$ is calculated, similarly to Step S102 in the first embodiment. In Step S203, a first peak level $Y_{p1}$, a second peak level $Y_{p2}$, and an average luminance level $J_{ave}$ are calculated for the first peak metering-area "A'1", the second peak metering-area "A'2", and the average metering-area "A'3" respectively.

In Step S204, the representative luminance level RI is calculated in accordance with the following formula.

$$RI = \alpha' \times J_{ave} + \beta' \times Y_{p1} + \gamma' \times Y_{p2} \tag{4}$$

Note that, $\beta'$ is larger than $\gamma'$.

As described above, when the tip portion 60 of the video-scope 50 faces to an axis direction of the organ, since an observed portion on the inner wall of an organ becomes close to the tip portion 60, the image is displayed at a position close to the peripheral area of the screen. Therefore, the luminance level becomes higher as the display position is close to the peripheral area. The first peak metering-area "A'1" and the second peak metering-area "A'2" are defined in accordance with the above characteristics associated with the luminance level. Then, the peak level $Y_{p1}$ is regarded as a more important level than the second peak level $Y_{p2}$.

In Steps 205 and 206, similarly to Steps S105 and 106 in the first embodiment, the representative luminance level RI is compared with the reference luminance level $Y_r$, and the diaphragm 16 is driven when the difference between the representative luminance level RI and the reference luminance level $Y_r$ is larger than the allowable difference "C".

Figure 7:
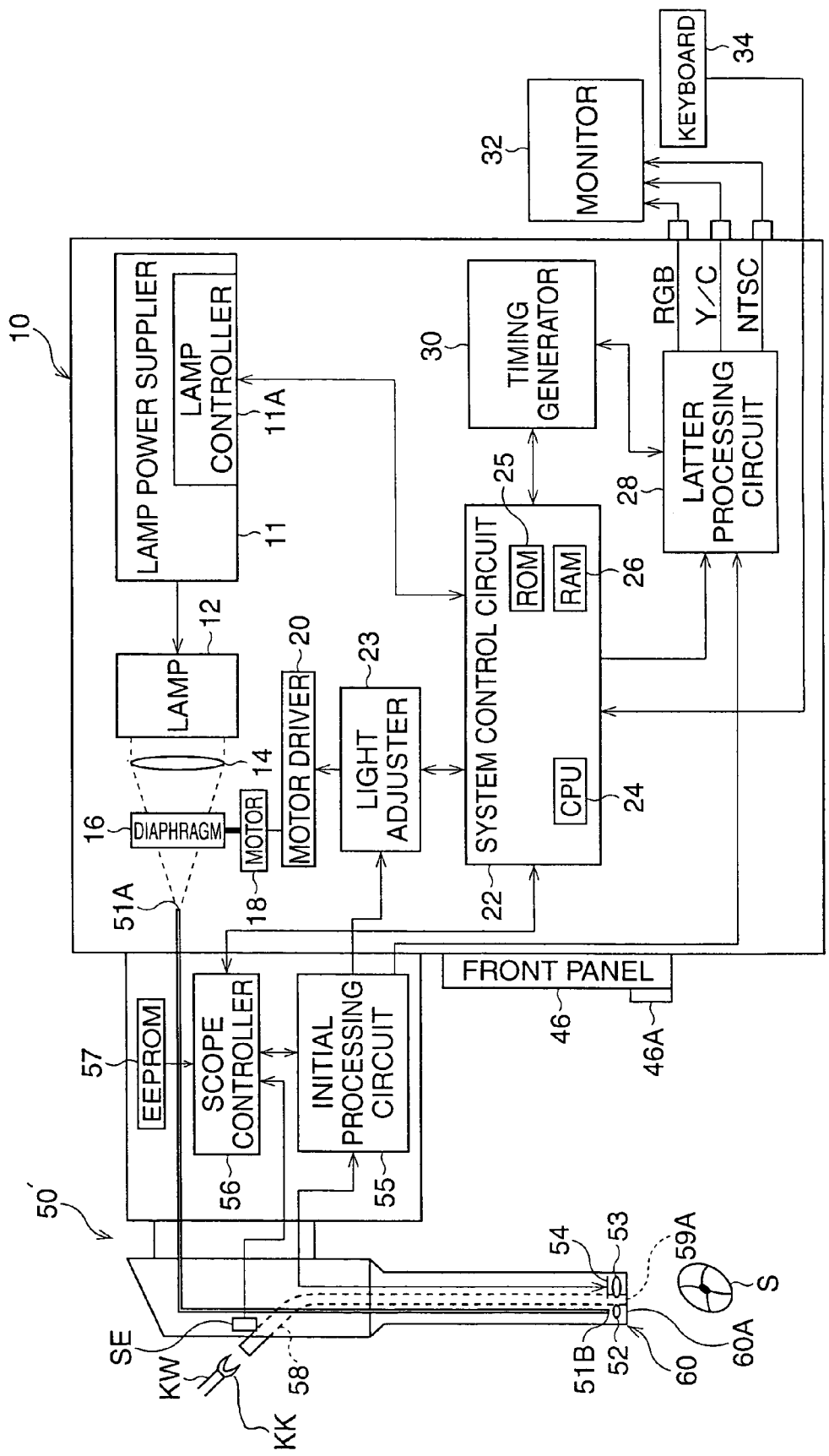
FIG. 7 is a block diagram of an electronic endoscope apparatus according to a third embodiment.
Figure 8:
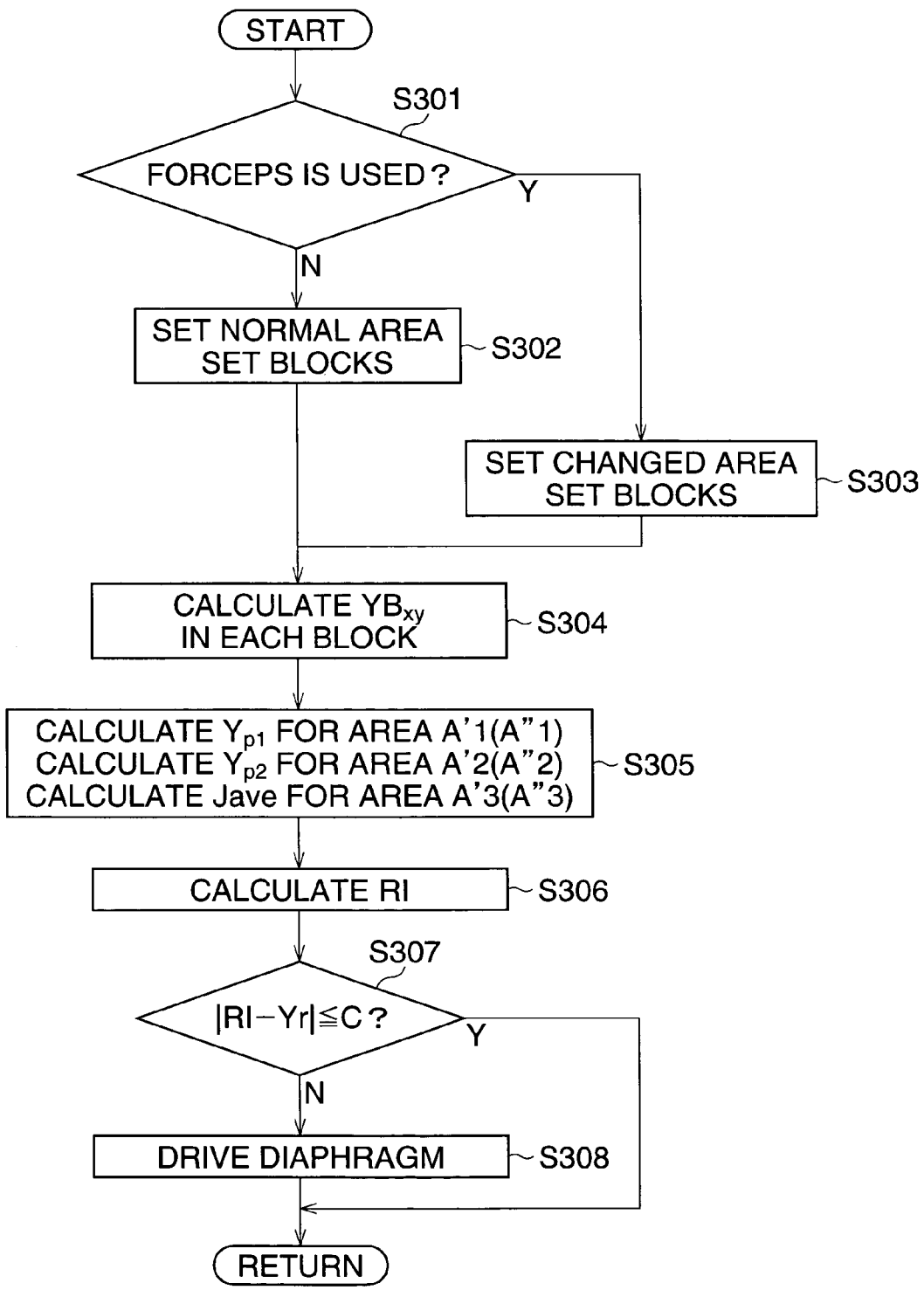
FIG. 8 is a flowchart of an automatic light-amount adjustment process according to the third embodiment.
Figure 9:
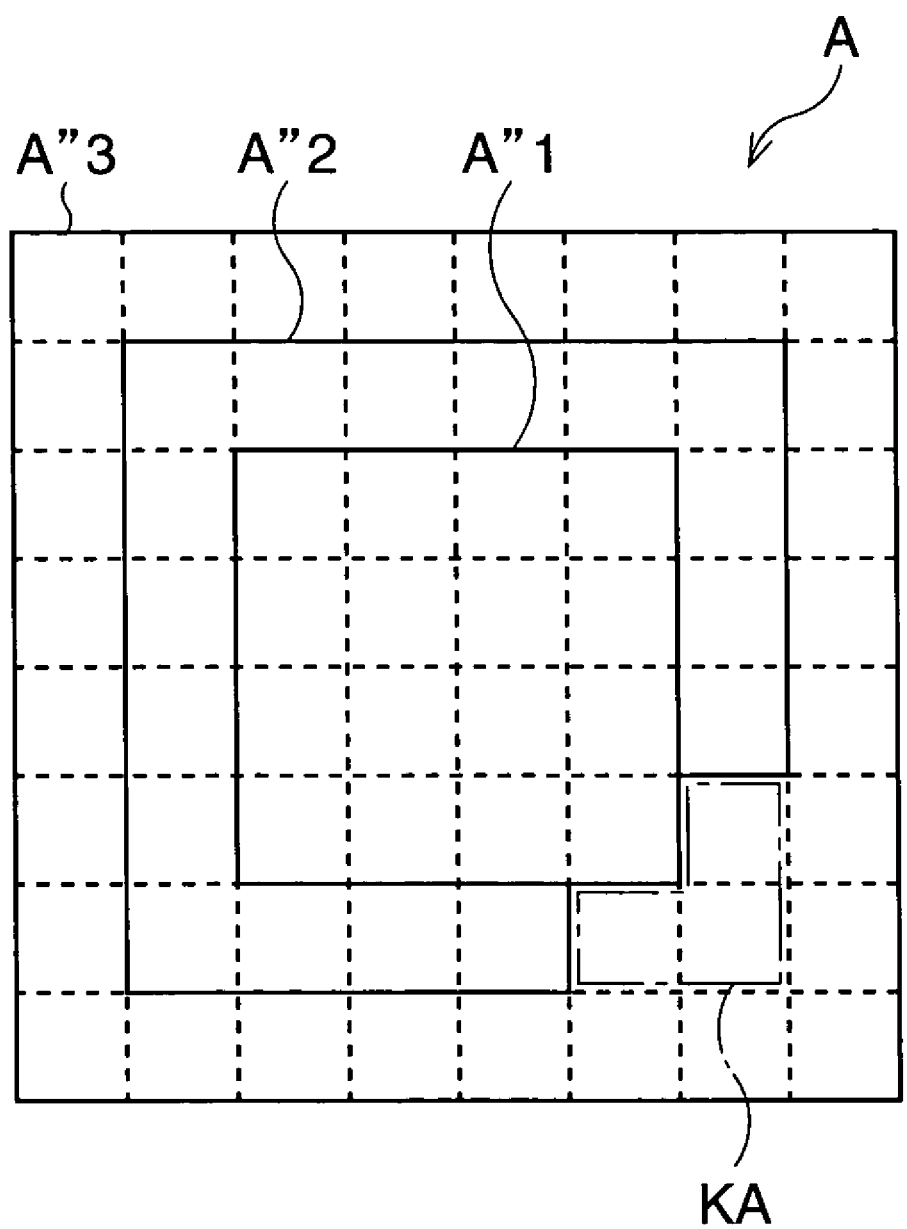
FIG. 9 is a view showing the metering-area of the observed image according to the third embodiment.

With reference to FIGS. 7 to 9, a third embodiment is explained. The third embodiment is different from the second embodiment in that the peak metering-area is changed in accordance with the use of forceps.

FIG. 7 is a block diagram of the third embodiment.

In the video-scope 50', a tool sensor SE is provided at the forceps tube 58, and the tool sensor SE is connected to the scope controller 56. The tool sensor SE detects the insertion of the treatment tool KW, and outputs a detecting signal to the scope controller 56. The scope controller 56 feeds the control signal, informing of the use of the forceps KW, to the system control circuit 22, and the detecting signal is fed from the system control circuit 22 to the light adjuster 23. In the EEPROM 57, position data of the forceps outlet 59A on the tip surface 60A is stored in advance. When the video-scope 50' is connected to the video-processor 10, the data including the position data of the forceps outlet 59A is fed to the system control circuit 22, and then the light adjuster 23.

FIG. 8 is a flowchart of an automatic light-amount adjustment process according to the third embodiment. FIG. 9 is a view showing a metering-area of the observed image.

In Step S301, it is determined whether the treatment tool KW is used. When it is determined that the treatment tool KW is not being used, that is the detecting signal is not input to the light adjuster 23, the process goes to Step S302. In Step S302, similarly to the second embodiment, the first peak metering-area "A'1", the second peak metering-area "A'2", and the average metering-area "A'3" are defined. After Step S302 is performed, the process goes to Step S304.

On the other hand, when it is determined that the treatment tool KW is being used, the process goes to Step S303. In Step S303, each block $B_{xy}$ is set, and a first peak metering-area A"1, a second peak metering-area A"2, and the average metering-area A"3 are defined. In this case, the second peak metering-area A"2 is defined by removing an L-shaped area (hereinafter, called "forceps area") KA from a rectangular-shaped form. The forceps area KA is defined in accordance with the position data stored in the EEPROM 57. The first peak metering-area A"1 and the average metering-area A"3 are defined similarly to that in the second embodiment.

When the forceps KW is used, the image of the forceps tip portion KK is displayed at the forceps area KW. At this time, the forceps area KA is not included in the first and second peak metering-areas "A"1" and "A"2". Consequently, even if the halation occurs in-the forceps area KA due to the metallic forceps tip portion KK, the peak level is not calculated on the basis of the halation. After Step S303 is performed, the process goes to Step S304.

The performance of Steps S304 to S308 corresponds to the performance of Step S202 to S206 of FIG. 5. Namely, average block-luminance-level $YB_{xy}$ is calculated, the first peak level $Y_{p1}$, the second peak level $Y_{p2}$, and the average luminance level $J_{ave}$ are calculated, and the representative luminance level RI is calculated. Then, the diaphragm 16 is driven in accordance with the difference between the representative luminance level RI and the reference luminance level $Y_r$.

Figure 10:
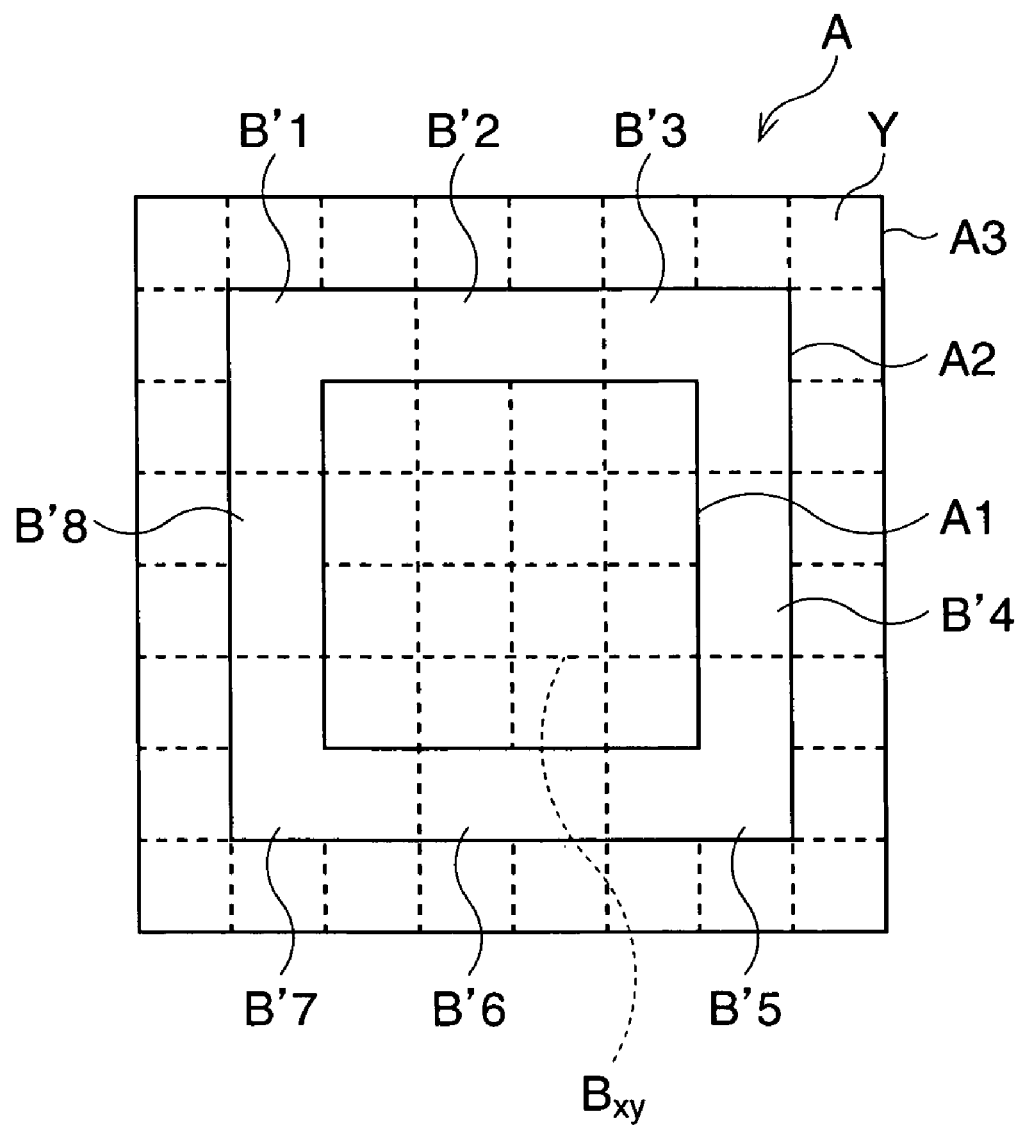
FIG. 10 is a view showing the observed image according to a fourth embodiment.

With reference to FIG. 10, the fourth embodiment is explained. The fourth embodiment is different from the second embodiment in that a plurality of different types blocks is defined.

FIG. 10 is a view showing the observed image according to the fourth embodiment.

The second peak metering-area A'2 is formed by 8 blocks B'1 to B'8, each of which is different from the block $B_{xy}$ shown in the first to third embodiments, with respect to the size or the number of pixels. The number of pixels in each of the blocks B'1 to B'8 is larger than that of the block $B_{xy}$.

The automatic light-amount adjustment process of this embodiment is substantially the same as the adjustment process according to the second embodiment. Namely, the average block-luminance-level is calculated for each block, and the first peak level $Y_{p1}$, the second peak level $Y_{p2}$, and the average luminance level $J_{ave}$ are calculated. Then, the representative luminance level RI is calculated, and the diaphragm 16 is driven in accordance with the difference between the representative luminance level RI and the reference luminance level $Y_r$. As the number of pixels in each of the blocks B'1 to B'8 is larger than that in the block $B_{xy}$, the average block-luminance-level for the blocks B'1 to B'8 is calculated without effect of the minute high-luminance-level area shown in FIG. 4B, so that the representative luminance level RI is calculated without the effect of the local high-luminance pixels.

The size of blocks B'1 to B'8 or the number of pixels of blocks B'1 to B'8 may be set to another size or number of pixels, which are different from the size and the number of pixels shown in FIG. 10. Further, the blocks B'1 to B'8 may be defined within the first peak metering-area "A'1", instead of the second peak metering-area "A'2".

Figure 11:
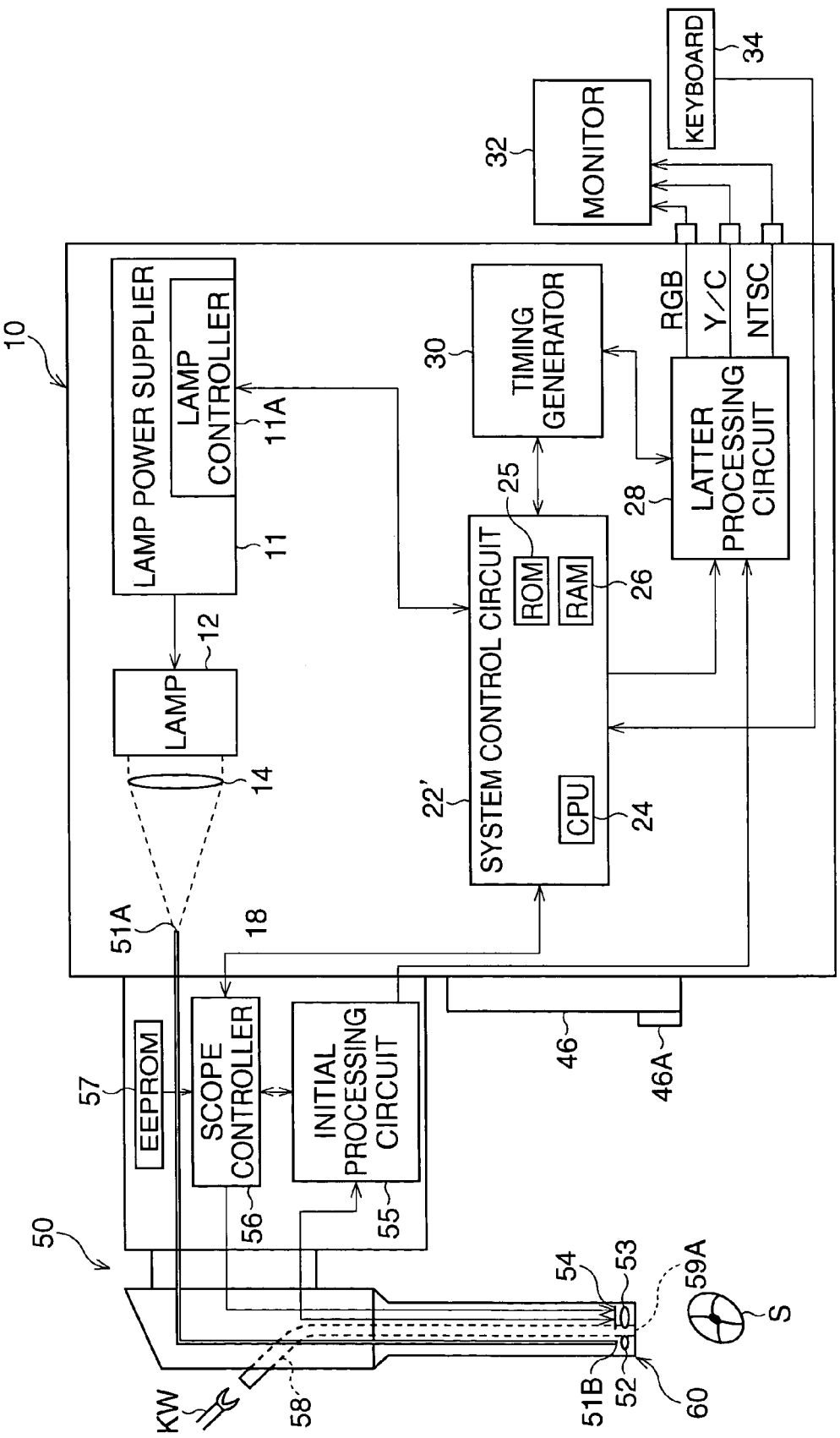
FIG. 11 is a block diagram of an electronic endoscope apparatus according to a fifth embodiment.
Figure 12:
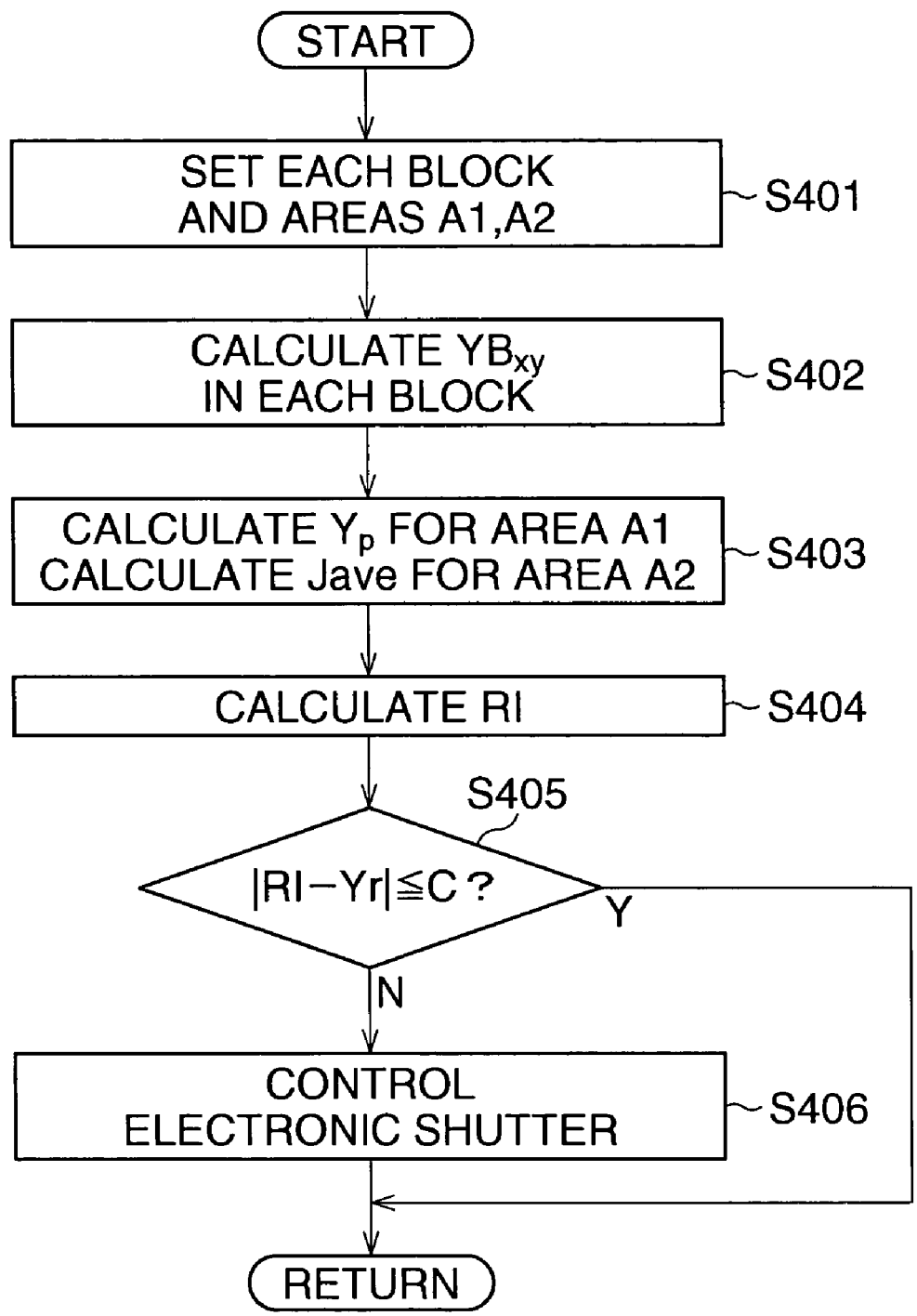
FIG. 12 is a view showing an automatic brightness adjustment process according to the fifth embodiment.

With reference to FIGS. 11 and 12, the fifth embodiment is explained. The fifth embodiment is different from the first, second, third, and fourth embodiments in that the charge-amount on the image sensor is adjusted by using the electronic shutter function, instead of the adjustment of light-amount using the diaphragm.

FIG. 11 is a block diagram of an electronic endoscope apparatus according to the fifth embodiment. In the fifth embodiment, the luminance signal is fed to the system control circuit 22', wherein the representative luminance level RI is calculated, and a control signal is output to the scope-controller 56 in accordance with the representative luminance level RI and the reference luminance level $Y_r$. The CCD 54 has an electronic shutter function, namely, the charge storage time is adjusted by a read-time control signal fed from the scope controller 56. When the control signal is fed from the system control circuit 22 to the scope controller 56, the read-time control signal is fed to the CCD 54, so that the charge storage time, namely, the shutter speed is adjusted such that the subject image maintains a proper brightness.

FIG. 12 is a view showing an automatic brightness adjustment process according to the fifth embodiment. The performance of Steps S401 to S405 is substantially the same as the performance of Steps S101 to S105 shown in the first embodiment. Then, in Step S406, the charge storage time control signal is fed to the CCD 54, and the charges are read from the CCD 54 at a given shutter speed so that the subject image maintains the proper brightness.

Finally, it will be understood by those skilled in the art that the foregoing description is of preferred embodiments of the device, and that various changes and modifications may be made to the present invention without departing from the spirit and scope thereof.

The present disclosure relates to subject matters contained in Japanese Patent Application No. 2002-317473 (filed on Oct. 31, 2002) which is expressly incorporated herein, by reference, in its entirety.

The invention claimed is:

1. An electronic endoscope apparatus having a video-scope with an image sensor and a video-processor, comprising:
   a light source that radiates light for illuminating a subject;
   a pixel luminance detector that detects a luminance level of each pixel in a plurality of pixels, that forms a subject image displayed on a display, in accordance with image-pixel signals read from said image sensor;
   a division setter that divides the subject image into a plurality of blocks composed of given pixels;
   an average block luminance calculator that calculates a plurality of average block-luminance-levels, each of which indicates a substantial average-luminance-level of the corresponding block, the average block-luminance-levels being calculated from a plurality of luminance levels of pixels arranged in the corresponding block;
   a peak-luminance determiner that compares the average block-luminance-levels with each other to determine a substantially maximum average block-luminance-level from the plurality of average block-luminance-levels as a peak luminance level;
   a representative luminance calculator that calculates a representative luminance level indicating a brightness of the subject image on the basis of at least the peak luminance level; and
   a brightness adjuster that adjusts the brightness of the subject image in accordance with the representative luminance level.

2. The electronic endoscope apparatus of claim 1, wherein the brightness adjuster adjusts an amount of light radiated from said light source toward the subject so as to maintain a proper brightness.

3. The electronic endoscope apparatus of claim 1, wherein the brightness adjuster adjusts an exposure time of the image sensor so as to maintain a proper brightness.

4. The electronic endoscope apparatus of claim 1, further comprising a peak metering-area setter that sets a peak metering-area around a center portion of the subject image,
   wherein said peak-luminance determiner determines the peak luminance level in accordance with blocks included in the peak metering-area.

5. The electronic endoscope apparatus of claim 4, further comprising a treatment tool detector that detects the use of a treatment tool utilizing a treatment tool tube provided in said video-scope,
   wherein said peak metering-area setter sets the peak metering-area so as to exclude a tool displaying area, in which a tip portion of the treatment tool is displayed.

6. The electronic endoscope apparatus of claim 1, further comprising:
   a peak metering-area setter that sets a peak metering-area around a center portion of the subject image;
   an average metering-area setter that sets an average metering-area in the subject image so as to include at least a peripheral portion of the subject image; and
   an average luminance calculator that calculates an average luminance level indicating a substantial average luminance level in accordance with blocks included in the average metering-area,
   wherein said peak-luminance determiner determines the peak luminance level in accordance with blocks included in the peak metering-area, and
   wherein said representative luminance calculator calculates the representative luminance level in accordance with the peak luminance level and the average luminance level.

7. The electronic endoscope apparatus of claim 6, wherein said representative luminance calculator multiplies the peak luminance level by a peak weighted coefficient and multiplies the average luminance level by an average weighted coefficient to obtain the representative luminance level.

8. The electronic endoscope apparatus of claim 1, further comprising:
   a peak metering-area setter that sets a first peak metering-area around a center portion of the subject image, and sets a second peak metering-area so as to surround the first peak metering-area,
   wherein said peak-luminance determiner determines a first peak luminance level in accordance with blocks included in the first peak metering-area, and determines a second peak luminance level in accordance with blocks included in the second peak metering-area, and wherein said representative luminance calculator calculates the representative luminance level in accordance with the first and second peak luminance levels.

9. The electronic endoscope apparatus of claim 8, wherein said representative luminance calculator multiplies the first peak luminance level by a first peak weighted coefficient and multiplies the second peak luminance level by a second peak weighted coefficient to obtain the representative luminance level, and wherein the first peak weighted coefficient is larger than the second peak weighted coefficient.

10. The electronic endoscope apparatus of claim 8, further comprising:

an average metering-area setter that sets an average metering-area in the subject image so as to include at least a peripheral portion of the subject image; and an average luminance calculator that calculates an average luminance level indicating a substantial average luminance level in accordance with blocks included in the average metering-area, wherein said representative luminance calculator calculates the representative luminance level in accordance with the first peak luminance level, the second peak luminance level, and the average luminance level.

11. The electronic endoscope apparatus of claim 8, wherein said division setter sets a first plurality of blocks composed of a first number of pixels, and sets a second plurality of blocks composed of a second number of pixels more than the first number of pixels, wherein the division setter sets the second plurality of blocks in one of the first peak metering-area and the second peak metering-area.

12. The electronic endoscope apparatus of claim 1, wherein said division setter sets the plurality of blocks such that each block has substantially the same size and substantially the same number of pixels.

13. The electronic endoscope apparatus of claim 1, wherein said division setter sets a plurality of different types of blocks, each of which is different from an other type of block with respect to at least one of the number of pixels and the size.

14. An automatic brightness adjusting apparatus for endoscope comprising:

a pixel luminance detector that detects a luminance level of each pixels in a plurality of pixels, that forms a subject image displayed on a display, in accordance with image-pixel signals read from an image sensor, which is provided in a video-scope;

an average block luminance calculator that calculates a plurality of average block-luminance-levels for a plurality of blocks, which is defined by dividing the subject image, each of the plurality of average block-luminance-levels indicates a substantial average luminance level of a block and is calculated from a plurality of luminance levels of pixels arranged in corresponding block;

a peak-luminance determiner that compares the average block-luminance-levels with each other to determine a substantially maximum average block-luminance-level from the plurality of average block-luminance-levels as a peak luminance level;

a representative luminance calculator that calculates a representative luminance level indicating a brightness of the subject image on the basis of at least the peak luminance level; and a brightness adjuster that adjusts the brightness of the subject image in accordance with the representative luminance level.

15. A method for adjusting a brightness of a displayed subject image obtained by using an electronic endoscope apparatus, comprising:

detecting a luminance level of each pixels in a plurality of pixels, that forms a subject image displayed on a display, in accordance with image-pixel signals read from an image sensor, which is provided in a video-scope;

calculating a plurality of average block-luminance-levels for a plurality of blocks, which is defined by dividing the subject image, each of the plurality of average block-luminance-levels indicates a substantial average luminance level of a block and is calculated from a plurality of luminance levels of pixels arranged in corresponding block;

comparing the average block-luminance-levels with each other to determine a substantially maximum average block-luminance-level from the plurality of average block-luminance-levels as a peak luminance level;

calculating a representative luminance level, which indicates a brightness of the subject image on the basis of at least the peak luminance level; and adjusting the brightness of the subject image in accordance with the representative luminance level.

* * * * *